July 22, 1969 R. S. MOORE Plant Pat. 2,909
MINIATURE ROSE PLANT
Filed Sept. 19, 1967
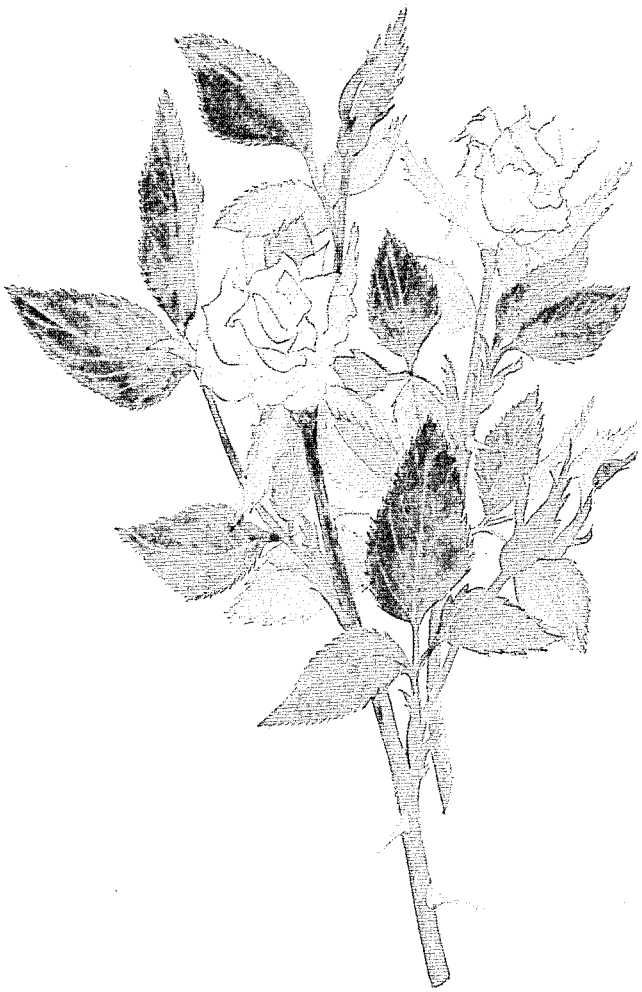
WITNESS
Jeanette Nunn Copley
INVENTOR
Ralph S. Moore

United States Patent Office

Plant Pat. 2,909
Patented July 22, 1969

2,909

MINIATURE ROSE PLANT

Ralph S. Moore, 2519 E. Noble Ave., Visalia, Calif. 93277

Filed Sept. 19, 1967, Ser. No. 668,976
Int. Cl. A01h 5/00
U.S. Cl. Plt.—7 1 Claim The present invention relates to a new and distinct variety of hardy, dwarf, bush type rose plant of the miniature class; the variety being primarily characterized—as to novelty—by bicolored buds and flowers, basically white with red to pink edges, the red coloring often blending into the white area on the upper surface of the petals but remaining essentially white with narrow red margin on the reverse side.

The variety is further characterized by:

An abundance of bloom, with flowers borne singly or in loose clusters of three or more to the stem. A plant which is moderately vigorous, of low rounded habit, with semi-glossy, medium green leaves. The plant which has a normal average height of about 10" at maturity, resembles the general plant habit of Easter Morning (Pl. Patent 2,177) miniature rose; the bud and flower being similar in form to Beauty Secret (plant patent applied for) but slightly smaller in size.

A plant which grows and blooms satisfactorily both in the greenhouse and outdoors; is a good plant for growing in pots; and provides excellent garden decoration as well as cut flowers.

The present variety of miniature rose was originated by me in my nursery, located at Visalia, Calif., under conditions of careful control and observation, as a cross between Little Darling (a floribunda rose, United States Plant Patent No. 1,581) as the seed parent, and Magic Wand (not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature.

Flowers:

*Continuity.*—Continuous.

*Fragrance.*—Very little or none.

Flowers borne: Singly and several together (3 to 5) on rather stiff medium length stems.

Quantity of bloom: Moderate to abundant both outside and in greenhouse.

Bud: Penduncle—medium length; slender; erect; light to medium green; few very short hairs. Before calyx breaks: size—small. Form—long, pointed; with foliaceous appendages on edges of sepals. Before calyx breaks: size—small. Form—pointed; with foliaceous appendages on surface of bud and foliaceous parts extending beyond the tip of the bud equal to one half or more of its length. Color—medium green (in greenhouse). As calyx breaks—color red at tip, shading into greenish white (or near white). Size—small. Form—long, with petals unfurling in classic Hybrid Tea rose style. Opening—opens well in all weather.

Bloom:

*Size when fully open.*—Small, 1¼".

*Petalage.*—Double, 18–25 petals, arranged regularly.

*Form.*—Cupped, with outer petals slightly reflexed.

Petals: Rather thick; stiff, satiny both inside and outside; waved or slightly twisted. Shape: outside petals broad lanceolate with acute tip; intermediate—broad lanceolate with acute tip; inside—lanceolate to broad lanceolate with acute tip.

Color: Newly opened flower from plant grown indoors (August 1967), Visalia, Calif.

*Outside petal.*—Outside surface—white or near white on entire surface with narrow edge of Fuchsine Pink 627; inside surface—white or near white with edge of Fuchsine Pink 627 and with the outer ½ (tip end) shaded in varying dilutions of the Fuchsine 627 color.

*Intermediate petal.*—Outside surface — same as above. Inside surface—same as above.

*Inside petal.*—Outside surface—same as above. Inside surface—same as above.

*General color effect newly opened flower.*—Red (or pink) and white. Three days open—essentially same effect but lighter color.

*Behaviour.*—Spent blooms may persist for a time before petals fall.

*Flower longevity* (August—in greenhouse—1967).—Bush or pot—4–6 days or longer. Outdoors (summer 4–6 days, in cooler spring or fall weather—6–10 days). Cut flowers at living room temperature—3–4 days.

Reproductive organs:

*Stamens.*—Abundane; arranged regularly about pistil.

*Filaments.*—Short.

*Pollen.*—Very little.

*Pistils.*—Short to average length and number.

*Styles.*—Medium length; bunched; greenish white.

*Stigma.*—Greenish white, some not complete.

*Ovaries.*—All enclosed in calyx.

*Hips.*—None.

*Sepals.*—Permanent; spear shaped, two smooth and three serrated, with foliar parts extending along edges.

*Seeds.*—None.

Foliage:

*Leaves.*—Compound of five leaflets (occasionally 3); abundant; small, leathery, semi-glossy.

*Leaflets.*—Shape—lanceolate, nearly oval; apex acute; base less acute; margin serrate. Color—medium to dark green; new growth often tinted bronze or reddish. Rachis—medium strength; upper side grooved; under side sparsely thorny. Stipules—relatively narrow, medium length; short points, turning out at angle of about 45 degrees.

Growth:

*Habit.*—Dwarf; bushy; rounded; much branched.

*Growth.*—Moderately vigorous.

*Canes.*—Medium, slender.

*Main stems.*—Color—medium green. Thorns—moderately thorny; slender; medium length; hooked slightly downward with sharp points; color—light to medium brown. Prickles—none. Hairs—none.

*Branches.*—Color—medium green. Thorns—moderately thorny; medium length; hooked slightly downward; sharp needle-like points; medium length oval base. Prickles—none. Hairs—none.

*New shoots.*—Color—medium green (often tinted bronze). Thorns—moderately thorny; very slender; hooked slightly downward; sharp points; base oval; color — reddish-green. Prickles — none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described, characterized by buds and flowers resembling the Beauty Secret miniature rose in general form, but of unique, for miniature roses, red and white combination coloring, resembling in this respect the hybrid tea rose Kordes' Perfecta (U.S. Plant Patent 1,604), the general color effect of the freshly opened flower being white with all petals edged red or deep pink; and further characterized by a plant of modest yet vigorous and compact growth, easy to propagate by budding or from cuttings, with small dark green foliage, an abundance of bloom borne almost continuously throughout the growing season with flowers borne singly and in loose small clusters.

No references cited.

ROBERT E. BAGWILL, Primary Examiner